(12) United States Patent
Strong (10) Patent No.: US 9,320,494 B2
(45) Date of Patent: Apr. 26, 2016

(54) CRADLE FOR AN ULTRASOUND PROBE

(71) Applicant: Best Medical International, Inc., Springfield, VA (US)

(72) Inventor: David Strong, Carmichaels, PA (US)

(73) Assignee: Best Medical International, Inc., Springfield, VA (US)

( * ) Notice: Subject to any disclaimer, the term of this patent is extended or adjusted under 35 U.S.C. 154(b) by 104 days.

(21) Appl. No.: 14/050,009

(22) Filed: Oct. 9, 2013

(65) Prior Publication Data

US 2014/0034800 A1 Feb. 6, 2014

Related U.S. Application Data

(63) Continuation-in-part of application No. 13/116,071, filed on May 26, 2011, now abandoned.

(51) Int. Cl.
*A61B 8/14* (2006.01)
*A61B 8/00* (2006.01)
*A61N 5/10* (2006.01)
*A61B 8/08* (2006.01)
*A61B 8/12* (2006.01)
*A61B 17/34* (2006.01)

(52) U.S. Cl.
CPC ............ *A61B 8/4209* (2013.01); *A61B 8/0841* (2013.01); *A61B 8/12* (2013.01); *A61B 8/4245* (2013.01); *A61N 5/1027* (2013.01); *A61B 8/085* (2013.01); *A61B 2017/3411* (2013.01); *A61B 2017/3413* (2013.01); *A61N 2005/1012* (2013.01); *A61N 2005/1058* (2013.01)

(58) Field of Classification Search
CPC ............ A61B 2017/3411; A61B 2017/3413; A61B 2019/5276; A61B 8/0841; A61B 8/085; A61B 8/12; A61B 8/4209; A61B 8/4245
See application file for complete search history.

(56) References Cited

U.S. PATENT DOCUMENTS

| | | | | |
|---|---|---|---|---|
| 4,957,215 A | * | 9/1990 | Evans et al. | 220/232 |
| 7,334,478 B2 | * | 2/2008 | Hwang | 73/618 |
| 2004/0143188 A1 | * | 7/2004 | Barzell et al. | 600/439 |
| 2007/0129634 A1 | * | 6/2007 | Hickey et al. | 600/439 |

OTHER PUBLICATIONS

Best Medical International, Inc., Best Total Solutions, advertising insert in Medical Physics Journal, and at shows, 2 pages, 2011.
Best Medical International, Inc., Simply the Best!, multi-product advertisement in "The Beam", American Society for Radiation Oncology (ASTRO), annual meeting, Miami Beach, FL, 1 page, Oct. 2-6, 2011.

(Continued)

*Primary Examiner* — Mark Remaly (57) ABSTRACT

A cradle for holding an ultrasound probe includes a base for securing to a stepper-stabilizer, roller-bearings supported on the base, and a probe-holder that rotates on the roller-bearings about a horizontal axis relative to the base. The probe-holder includes a front yoke and a rear yoke, with a yoke retainer supporting the front yoke. A pivot side rail and a lock side rail span rigidly between the front yoke and the rear yoke. A locking knob is captured to the lock side rail to prevent the locking knob from detaching. A latch hinged to the pivot side rail is engaged by the locking knob for securement over the probe. A detent ensures 90-degree alignment of the yoke retainer to the base. The rollers rotatably support the yoke retainer and the rear yoke, and further rotation of the front yoke enables a further adjustment to calibrate the cradle.

20 Claims, 7 Drawing Sheets

(56) References Cited

OTHER PUBLICATIONS

Brachytherapy Services Inc. (BSI), data sheet, 6000 Precision Stablilzer and STP 110 Precision Stepper, American Society for Radiation Oncology (ASTRO), 51st Annual Meeting, Chicago, Illinois, 1 page, Nov. 1-5, 2009.

Brachytherapy Services Inc. (BSI), poster, 6000 Precision Stablilzer and STP 110 Precision Stepper, American Society for Radiation Oncology (ASTRO), 51st Annual Meeting, Chicago, Illinois, 1 page, Nov. 1-5, 2009.

Best nomos®, STP 110 PrecisionTM Stepper, Instructions for Use, v.12.2010, 20 pages, 2010.

Best Medical International, Best NOMOS, data sheet, 6000 Precision Stablilzer and STP 110 Precision Stepper, American Society for Radiation Oncology (ASTRO) 52nd Annual Meeting, San Diego Convention Center, San Diego, California, 1 page, Oct. 31, 2010 to Nov. 4, 2010.

Best Medical International, Best NOMOS, poster, 6000 Precision Stablilzer and STP 110 Precision Stepper, American Society for Radiation Oncology (ASTRO) 52nd Annual Meeting, San Diego Convention Center, San Diego, California, 1 page, Oct. 31, 2010 to Nov. 4, 2010.

\* cited by examiner

CRADLE FOR AN ULTRASOUND PROBE

CROSS REFERENCE TO RELATED APPLICATION

This application is a continuation-in-part of U.S. patent application Ser. No. 13/116,071, filed on May 26, 2011, hereby incorporated herein by reference in its entirety.

FIELD OF THE INVENTION

The invention relates to a cradle for holding an ultrasound probe, as may be used in brachytherapy.

BACKGROUND

The concept of insertion of radioactive sources into the prostate for the treatment of prostate cancer has a long history. Many patients with prostate cancer were treated by this method in the 1960s and 1970s. At that time the radioactive seeds were placed in the prostate through an open surgical incision in the lower abdomen. Because of the uncertainty of seed placement by this method, this technique was abandoned.

By the late 1980s, technologic and scientific advances in transrectal ultrasound imaging revived interest in seed implantation for the treatment of prostate cancer. Transrectal ultrasound probes make possible real-time interactive placement of radioactive seeds into the prostate. The doctor inserts an ultrasound probe into the rectum and attaches it to a stabilizing device which secures the toot to a table or chair for the duration of the treatment. In addition, 3-D simulation software allows accurate determination of the doses delivered to the prostate and surrounding structures, such as the bladder, urethra and rectum. These tools have permitted the refinement of interstitial brachytherapy for prostate cancer and have resulted in more accurate methods of delivering doses to the prostate gland.

The stepper is a lightweight, precision stepping device. The steppers modular design is adaptable to a variety of transrectal transducers. The stepper features easy-to-read marking scales.

A cradle may be connected to the stepper. The cradle holds an ultrasound probe in a fixed position. When the cradle is fixed to the stepper, the stepper allows a gentle fixed distance movement proximally and distally of an ultrasound probe held in the cradle. Each step taken by the stepper is a precise measured movement. The cradle will move with the ultrasound probe depending on the movement of the stepper.

In an ultrasound imaging system with an endorectal ultrasound probe, the rectal probe must be able to image in transverse section at least. It is advantageous to use a multi-plane probe to visualize any longitudinal plane in order to see the needle path. The frequency of the probe should range between 5 and 8 MHz in order to achieve the necessary spatial resolution as well as the necessary penetration depth.

The precision stepper enables the user to advance and retract an endorectal ultrasound probe in the rectum to image the prostate. The endorectal (ER) probe is inserted into and fixed to the stepper and positioned by moving the stepper/probe combination. Any endorectal (ER) probe from any producer can be fitted to the stepper. A movable length of the probe with the stepper can be 100 millimeters (mm). A scale for position recognition can have a step width of 2.5 mm or 5 mm selectable, as well as free analog movement in and out of the rectum. Additional free analogue movement of the probe to define the exact starting point for stepwise movement can be 50 mm. Also, a template is movable (100 mm) in the direction parallel to the ER probe's long axis and can be fixed in any position.

A needle guide grid system is provided for brachytherapy needles. The needle guide system can have a matrix of 13 times 13 individual channels (all channels for 18 Gauge needles-standard). The needle guide system can have two nomenclatures (reversible) of the needle channel rows 1 to 7 (every second row with a number, front side of the template) or rows 0 to 12 (every row with a number, back side of the template). Also, the row spacing can be 5 mm in both cases. The needle guide system can also have two nomenclatures (reversible) of the needle channel columns: A to G (every second row with a letter, front side of the template) or A to M (every row with a letter, back side of the template). Column spacing can be 5 mm in both cases. The template is made of a material used for implants, and thus is fully bio-compatible.

A device that supports the stepper is the stabilizer. The stabilizer is connected to the guide rails of an operating room (OR) table by a specific table holder, for example. The stabilizer and stepper can be moved and positioned manually by the integrated handle, as well as can be fixed or loosened in its position in space.

However, recently there have been many different problems with the cradle. The problems with the cradle are that the ultrasound probe will not stay in a fixed position and, therefore, not allowing proper alignment of the needle grid to the image on the display screen. Another problem with the cradle is that the cradle does not allow for proper 90° degree calibration, thereby not providing a repeatable, fixed reference point to medical personnel. Another problem with many cradles relates to needle path verification. The needle path verification can be time consuming when the medical personnel have to calibrate the cradle holding the ultrasound probe to the needle grid. Many cradles require that the medical personnel remove or adjust the ultrasound probe, which is very time consuming and does not provide efficient medical treatment. Therefore, there is a need in the art to improve the calibration of the ultrasound probe and the needle path verification. Furthermore, it would be desirable to allow medical personnel to improve patient treatment time, and provide an efficient treatment modality for medical personnel.

SUMMARY OF INVENTION

According to one general aspect, a cradle for holding a probe is provided that is used to image a patient prior to and during medical procedures, where the cradle is connected to a stepper-stabilizer via a plurality of cradle fix holes. The cradle further includes a locking knob attached to a side of the cradle for tightening and loosening a latch holding the ultrasound probe. Further, a capture knob is mounted inside the locking knob to prevent the locking knob from detaching from the cradle. The latch is connected on top of the cradle to wrap over and on top of the ultrasound probe. A probe lock fixer, e.g. a pressure pad, formed on the latch fastens to the probe when the latch is in a closed position, which results in anchoring the ultrasound probe inside a probe space. A micro-adjuster is connected to both sides of the cradle, and allows for refined adjustment in angular rotation around the horizontal axis of the cradle. Roller-bearings attached between the cradle base and the cradle allow for smooth angular rotation on the horizontal axis.

The micro-adjuster allows the cradle to be calibrated to a predetermined angle with or without the probe affixed to cradle. The micro-adjuster allows medical personnel to adjustably rotate the cradle a maximum of 10° (+/−) via mechanically altering the cradle yoke and side-railing assembly rotatably, independently of a yoke retainer, which can be precision-aligned by way of a detent to the cradle base.

The micro-adjuster desirably utilizes bearings assembled to the yoke retainer for free rotation of the front yoke with respect to the yoke retainer. Control of the front yoke rotation by the bearings may be altered by a screw or a release button for quick calibration.

The cradle holds an ultrasound probe that is held in place by a latch that is set to lock by tightening the locking knob. The latch pushes down on the probe via the pressure pad formed on the latch. The pressure pad has a sloping, asymmetric cross-section, which achieves mechanical advantage in securing the ultrasound probe in the cradle. Once secured, alignment of the ultrasound probe image can be refined using the micro-adjuster capabilities. The pressure pad further features a concave, curved surface for engaging the ultrasound probe. In this fashion, the concave, curved surface allows maximizing a surface area of the pressure pad to engage the probe, thereby resulting in no further angular movement of the probe.

DETAILED DESCRIPTION

The invention generally relates to the treatment of prostate cancer by using a stepper-stabilizer to image the patient prior to and while inserting radioactive seeds for dose treatment.

Figure 1:
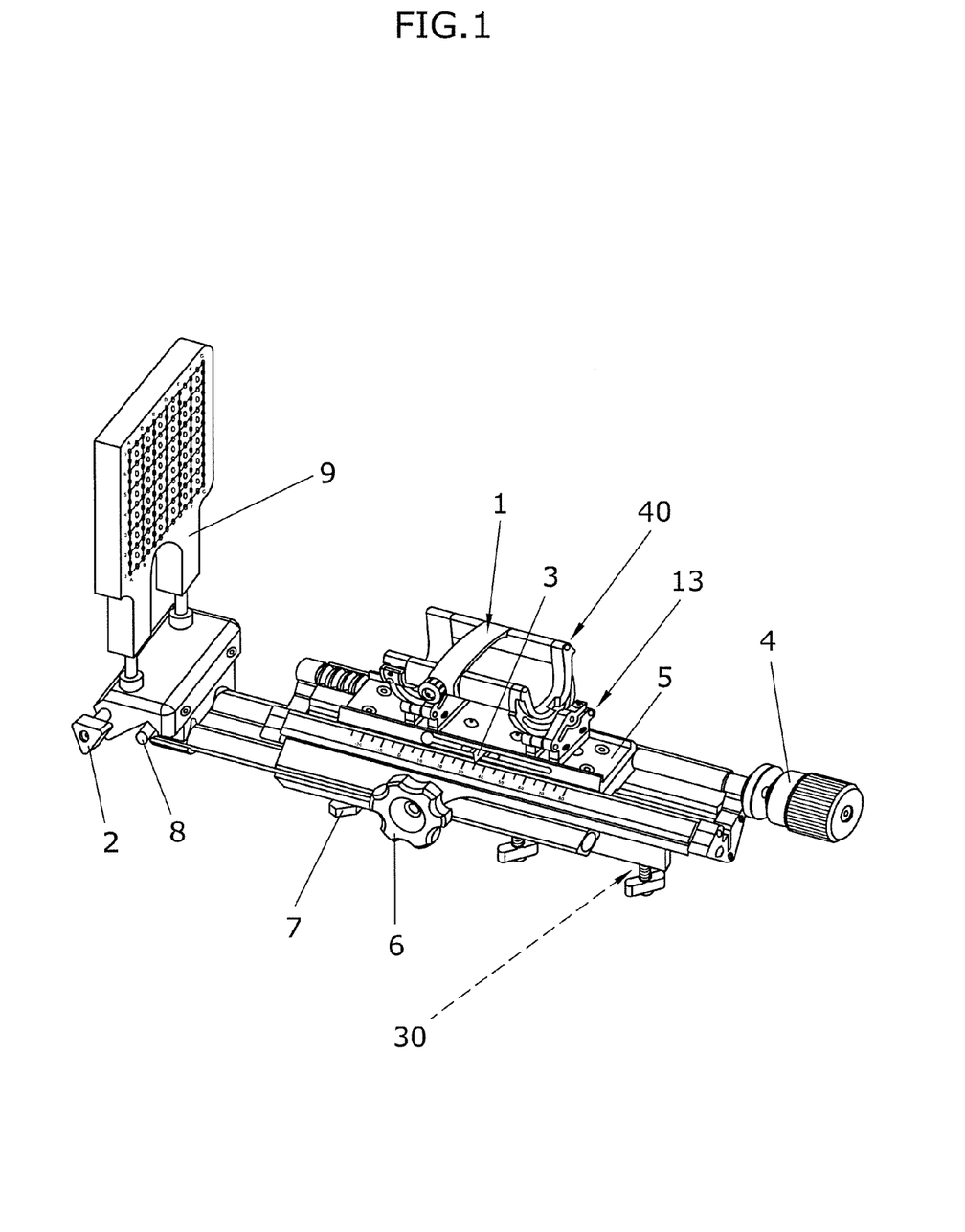
FIG. 1 is an environmental view of an exemplary cradle according to the present invention, shown mounted on a stepper supporting a needle guide template.

FIG. 1 illustrates a top view of a cradle 1 attached to a stepper 5. The cradle 1 includes a probe-holder 40 and a cradle base 13 supporting the probe-holder 40. The stepper 5 is a piece of hardware that is used to connect to a stabilizer generally indicated at the numeral 30. This overview illustrates the correlation of the cradle 1 to the stepper 5. Further, attached to the stepper 5 is a needle guide template 9. The needle guide template 9 is used to provide the location of brachytherapy needle strands inserted into the human body while being imaged on the patient, as by a Best NOMOS® Sonalis™ system, for example. The needle guide template 9 is fixed on the system by way of a template locking knob 2. The template locking knob 2 allows a medical assistant to fix the needle guide template 9, thus allowing calibration between the needle guide template 9 and an ultrasound image provided by the ultrasound probe. It is important that the ultrasound probe be precisely aligned with the needle guide template 9 guide as illustrated on an imaging device (not shown). However, there can still be problems in the prior art with alignment because of the misalignment of cradles and probes. This can result in placing a radioactive seed in the wrong location, or not as directed by the treatment plan.

As shown in FIG. 1, the stepper 5 has a baseline marker 3. The baseline marker 3 measures the depth of the probe during insertion into the human body. This allows medical personnel to insert the probe to a specific depth in the human body to image a front, middle, or back part of the prostate, for example. The baseline marker 3 can be adjusted using a fine-tuning knob 4, which allows medical personnel to calibrate the stepper distance prior to inserting the probe into the human body. The stepper 5 can be secured to a stabilizer by way of tightening knobs on the base of the stepper 5. A stepper knob 6 is used to move forward and backwards the stepper 5, the cradle 1, and an ultrasound probe secured in the cradle 1. Wing nuts 7 securely latch the stepper 5 to rods on which a needle guide template support is located. Also, the wing nuts 7 can be loosened so that mounting screws can slide onto a mounting bracket of the stabilizer, generally indicted at the numeral 30 in FIG. 1. The needle guide template support is secured to the rods by knurled knobs, of which only one, a left-side knob 8, is shown in FIG. 1. Grommets on the needle guide support receive posts on the needle guide template 9.

Although major adjustments of the system and component alignment are afforded, prior art devices do not allow fully for precise calibration of an ultrasound probe supported in a prior art cradle. However, the cradle 1 of the present invention is designed to allow for micro-adjustments. Further, the stepper 5 and the needle guide template 9 support and allow for horizontal and vertical needle path adjustments by changing the needle guide template 9 location to match an on-screen grid projected over an image generated by an ultrasound probe. When such horizontal and vertical adjustments are made, there may remain alignment artifacts in the screen display. Such alignment artifacts may result from manufacturing factors inherent to the ultrasound probe, for example. System and component alignment, and removal of alignment artifacts, may be accomplished using the micro-adjustment aspects included on the cradle 1 of the present invention.

Figure 2:
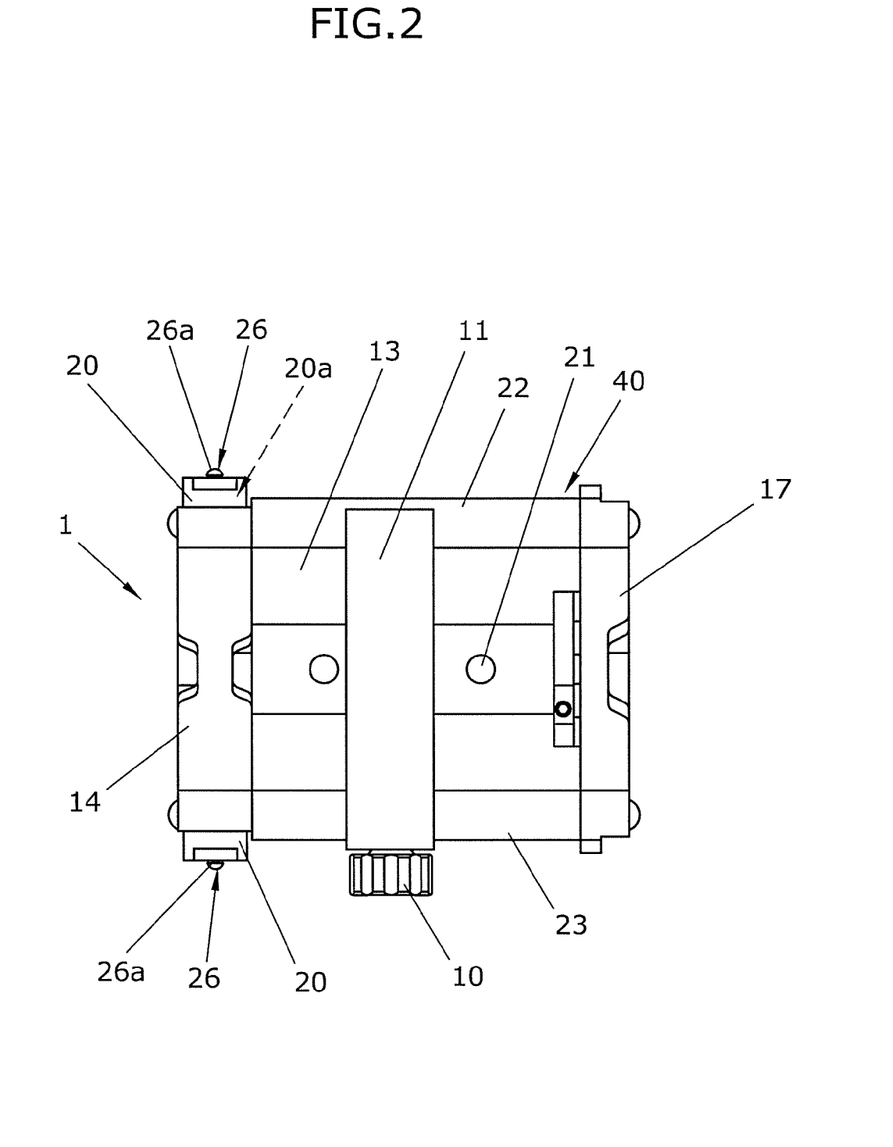
FIG. 2 is a top view from above of the cradle of FIG. 1.

FIG. 2 illustrates a top view of the cradle 1. The cradle 1 includes a locking knob 10. The locking knob 10 secures a latch 11, which can be fixed over an ultrasound probe to be secured in the cradle 1. The latch 11 is pivot-mounted on a right side or pivot side rail 22. As discussed further below, the latch 11 allows for the probe to be fixed securely, whereas prior cradles had problems with ultrasound probes sliding out, or otherwise becoming loose. Also shown in FIG. 2, is a micro-adjuster 20, including micro-adjuster bearings 20a, discussed further below. The cradle 1 may be attached to the stepper 5 by screws secured via cradle-fix holes 21 formed through the cradle base 13.

Figure 3:
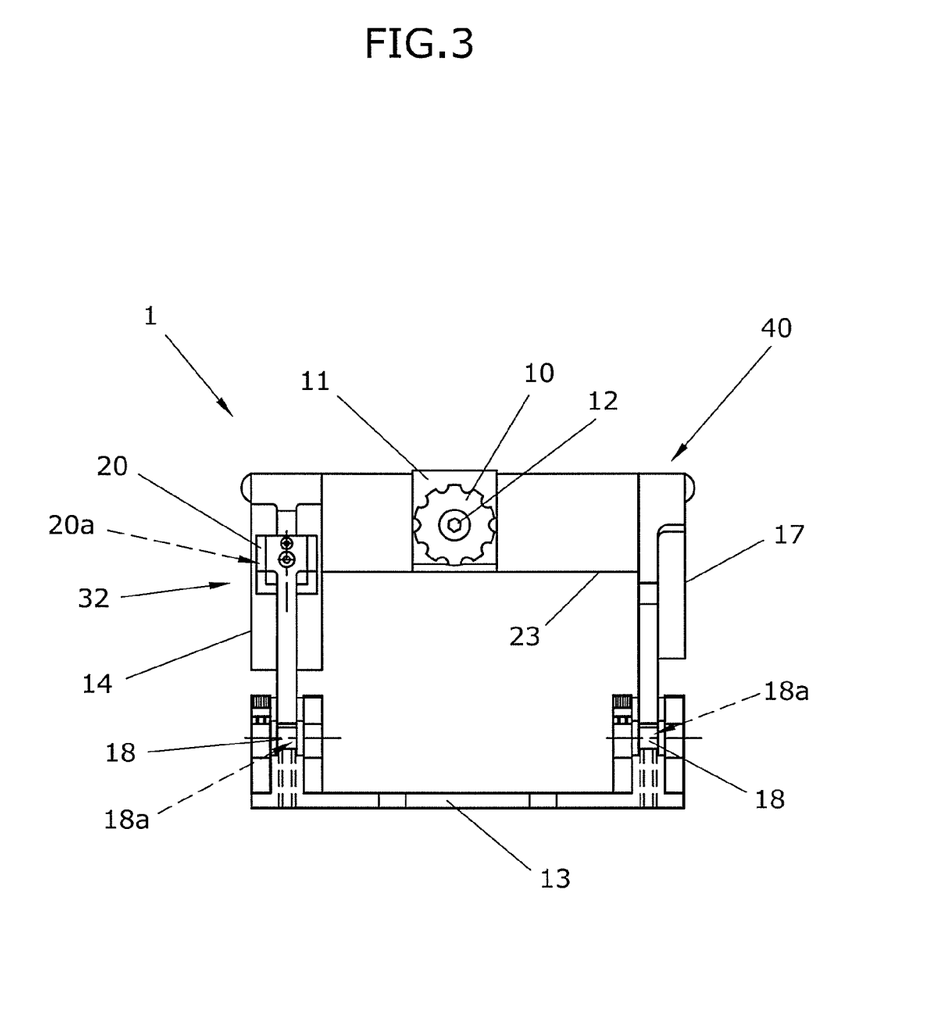
FIG. 3 is a front view of the cradle of FIG. 1.

FIG. 3 illustrates a left-side view of the cradle 1, shown in elevation. The locking knob 10 is fixed against loss with a capture knob 12. The capture knob 12 is assembled to a left side rail 23 of the cradle 1, typically using a high-strength adhesive, while keeping locking knob 10 free to turn.

Referring further to FIGS. 2, 3, 4 and 6, shown are the probe-holder 40 including a front yoke 14, a yoke retainer 24 and a rear yoke 17. The front yoke 14 and the rear yoke 17 are connected rigidly by the right side rail 22 and the left side or lock side rail 23. The front yoke 14 is assembled to the micro-adjuster 20, including the micro-adjuster bearings 20a, to form a front yoke assembly 32, described further below. The front yoke assembly 32, including the yoke retainer 24 and the front yoke 17, and the rear yoke 17 are rotatably supported on various rollers 18, such as a plurality of rollerbearings 18a, for rotation of the probe-holder 40 with respect to the cradle base 13. The yoke retainer 24 and the rear yoke 17 of the probe-holder 40 can rotate relative to the cradle base 13 in a first range of angular rotation for a maximum of 180 degrees (+/−90 degrees) by the rollers 18 associated with the cradle base 13, such as the plurality of roller-bearings 18a. The micro-adjuster 20, including the micro-adjuster bearings 20a allow for rotational movement of the front yoke 14 and the rear yoke 17, affording refined adjustments of the cradle 1 for a further adjustment through approximately 15° (7.5°+/−), in a second range of angular rotation of the front yoke 14 and the rear yoke 17 of the probe-holder 40 relative to the cradle base 13, the second range of angular rotation being less than the first range of angular rotation. As explained in further detail below, the micro-adjuster 20, including the micro-adjuster bearings 20a is used for the second adjustment to further calibrate the cradle 1, after the probe-holder 40 has been precision-located by detent in a 90-degree perpendicular plane for a first adjustment to calibrate the cradle 1 for a medical procedure, to account for any remaining misalignments when correlating with images from ultrasound probes secured in the cradle 1. The micro-adjuster 20, including the micro-adjuster bearings 20a, allow medical personnel to change a beam plane alignment slightly to correct calibration errors, to provide a second adjustment to further calibrate the cradle 1, after the first adjustment, for a medical procedure. Specifically, some ultrasound probes are potted incorrectly during manufacture with crystal misalignment. Therefore, the micro-adjuster 20, including the micro-adjuster bearings 20a, allow for correction of manufacturing defects by moving the ultrasound probe, secured within the cradle 1, independent of a precise, 90-degree alignment obtained from a center detent, as discussed herein.

Figure 4:
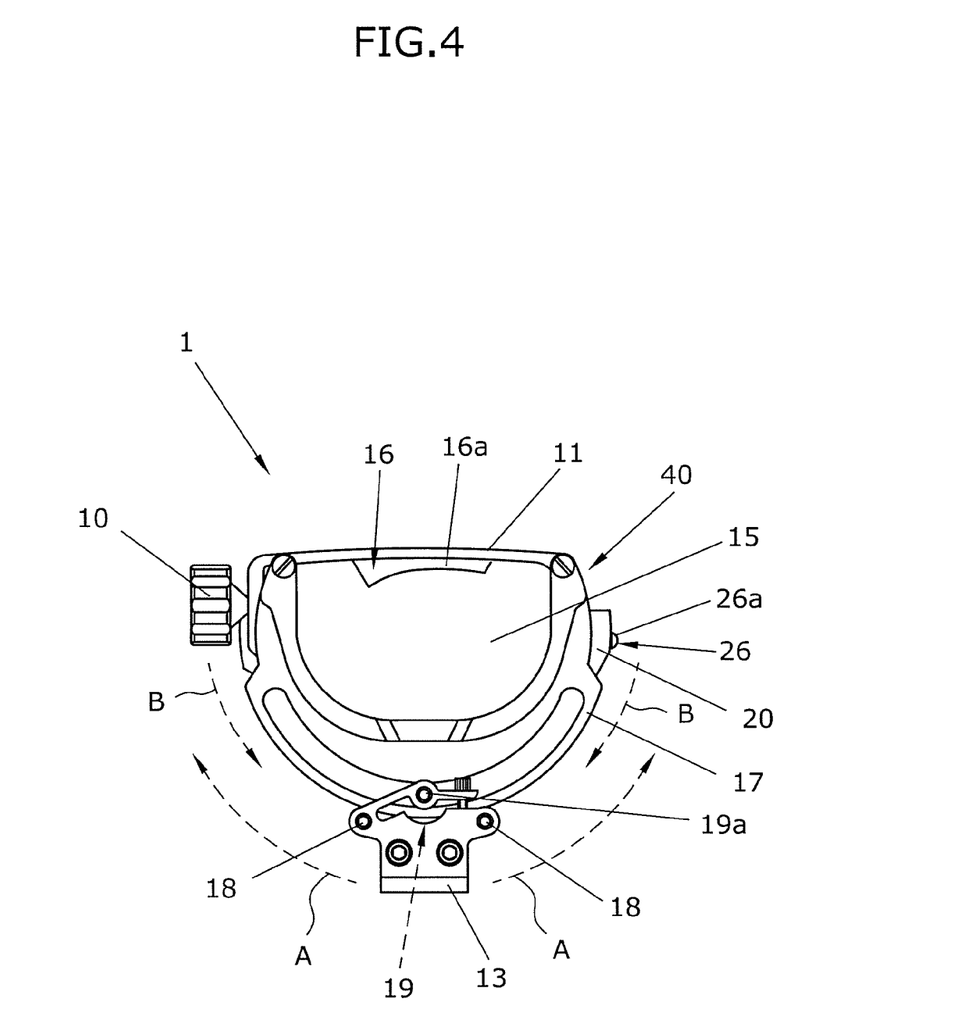
FIG. 4 is a front view of the cradle of FIG. 1.
Figure 6:
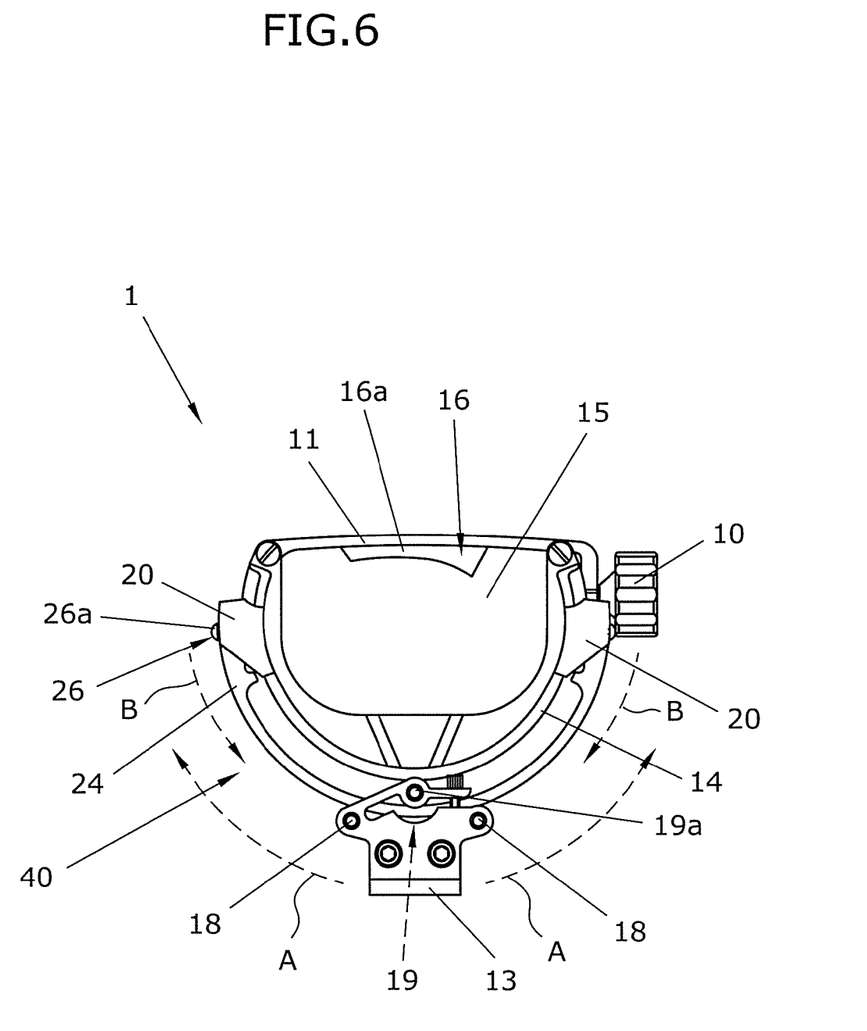
FIG. 6 is a rear view of the cradle of FIG. 1.

Referring to FIGS. 4 and 6, FIG. 4 illustrates a front-view and FIG. 6 illustrates a rear view of the cradle 1. The probe-holder 40 of the cradle 1 includes a probe space 15, for receiving a probe, and includes the front yoke 14 and the rear yoke 17 and the yoke retainer 24 that supports the front yoke 14. The probe-holder 40 can also include the latch 11, the locking knob 10 and the capture knob 12, as well as can include the pivot side rail 22 and the lock side rail 23. The latch 11 can open and close over a given ultrasound probe when the probe is positioned in the probe space 15 of the probe holder 40 of the cradle 1. The selected ultrasound probe may be placed into the probe space 15 of the probe-holder 40 and enclosed by the latch 11. The latch 11 has a probe-lock-fixer 16, such as a pressure pad 16a, that is attached to the latch 11. The probe-lock-fixer 16 is used to hold the probe in place when the probe is positioned in the probe space 15 of the cradle 1. While prior art cradles would hold the probe, however, during medical procedures, the probes would be known rotate a few degrees, which affects the imaging quality and device alignment during the procedure. Therefore, the probe-lock-fixer 16 is designed to hold the probe in a fixed position, without causing rotational plane movement. Advantageously, the probe-lock-fixer, such as the pressure pad 16a, has an eccentric, concave profile, such as illustrated in FIGS. 4 and 6. Such profile of probe-lock-fixer 16, such as of the pressure pad 16a, affords a mechanical advantage in securing the chosen ultrasound probe in the probe space 15 of the probe holder 40 of the cradle 1.

The cradle base 13 supports and houses a series of the rollers 18, such as the plurality of roller-bearings 18a. The rollers 18 allow for a smooth, rotational movement of the probe when held in a fixed position in the probe space 15 of the probe-holder 40 of the cradle 1.

Figure 5:
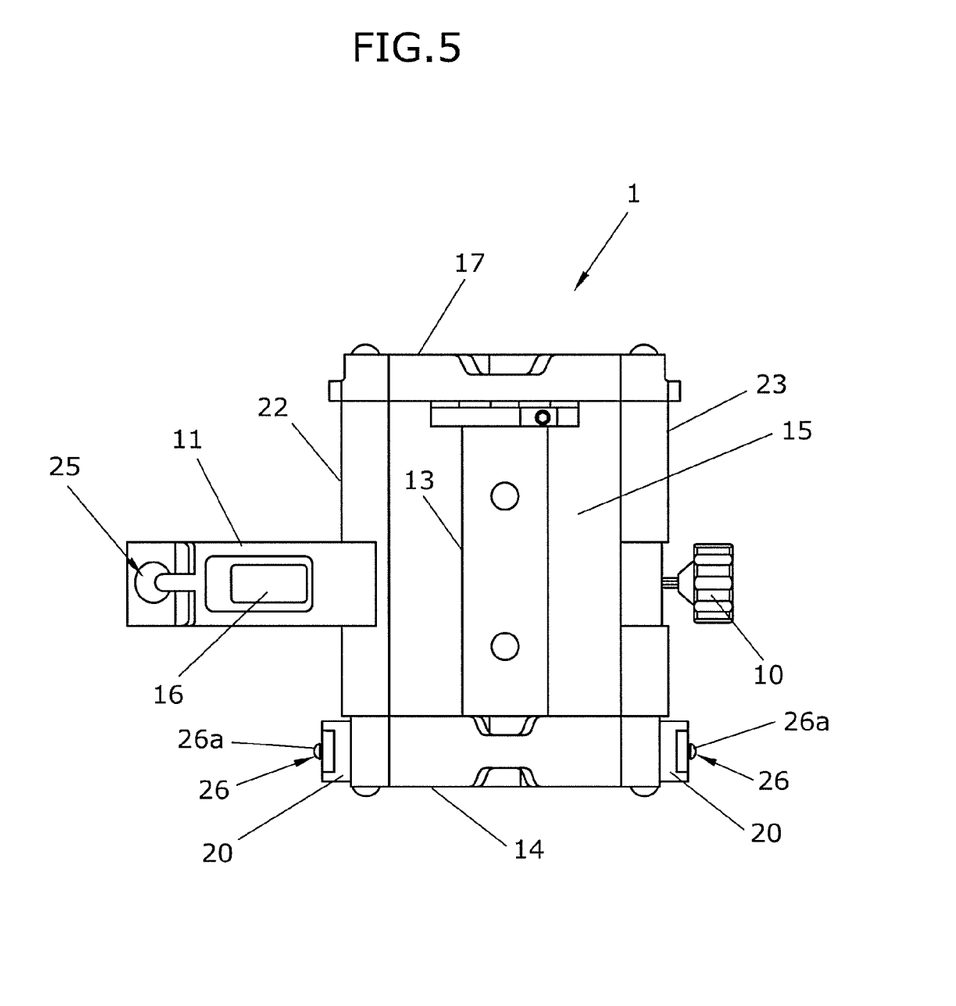
FIG. 5 is a top view from above of the cradle of FIG. 1 with a latch of the cradle unsecured and in an open position.

FIG. 5 is a top view of the cradle 1 with the latch 11 open to show the probe space 15. The selected ultrasound probe is placed into the probe space 15 and closed over by the latch 11. The latch 11 has a cone-shaped cavity 25 that accepts the correspondingly cone-shaped locking knob 10. The locking knob 10 cooperates with the cone-shaped cavity 25, which allows for self-tensioning of the latch 11 that holds the ultrasound probe securely in place.

FIG. 6 illustrates a right-side rear view of the exemplary cradle 1 with the latch 11 in a closed position. The probe-lock-fixer 16, such as the pressure pad 16a, is designed in a concave, eccentric fashion, as noted above. Such design of the probe-lock-fixer 16 allows for maximizing a surface area of the probe-lock-fixer 16 to contact the probe, when the probe is held in the probe space 15 by the probe-lock-fixer 16 being positioned against the ultrasound probe, to restrict angular movement of the probe when the ultrasound probe is positioned in the probe space 15.

Figure 7:
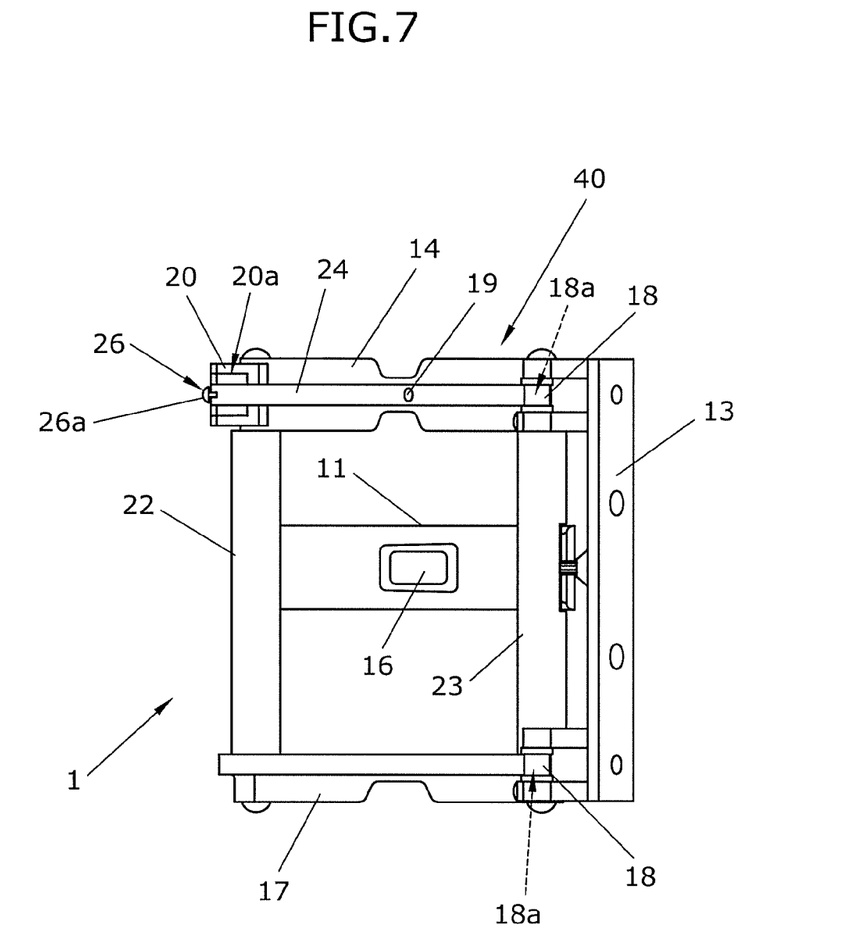
FIG. 7 is a bottom view of the cradle of FIG. 1, with a base of the cradle rotated to the right as illustrated in FIG. 7.

FIG. 7 illustrates a bottom-view of the cradle 1. As the yoke retainer 24 and the rear yoke 17 rotate on the rollers 18, such as on the roller-bearings 18a, and move from one side to another side, the probe holder 40 cradle base 13 slides over a locker, such as a detent, 19 associated with the cradle base 13. As illustrated in FIGS. 4, 6 and 7, the locker, such as the detent, 19 cooperates with a spring-loaded ball bearing 19a supported on the cradle base 13, and is used to orient repeatably and precisely the yoke retainer 24 with respect to the cradle base 13, such as in a 90-degree position, for the first adjustment to position the probe-holder 40 at a predetermined position at a predetermined angle relative to the cradle base 13 by the probe-holder 40 engaging the locker, such as the detent, 19. As illustrated in FIGS. 3-6, the rollers 18, such as including the plurality of roller-bearings 18a, rotatably support the probe-holder 40 on the cradle base 13 and are configured to enable the angular rotation in the first range of angular rotation, the first range of angular rotation being indicated by the dashed arrowed lines A, for the first adjustment to calibrate the cradle 1 for a medical procedure. As illustrated, the rollers 18, such as including the plurality of roller-bearings 18a, are associated with the cradle base 13, the yoke retainer 24 and the rear yoke 17. Also, the cradle base 13 and the probe-holder 40 are configured to enable the yoke retainer 24 and the rear yoke 17 to rotate in the first range of angular rotation to adjust a position of the probe-holder 40 for a medical procedure. However, there may be misalignment issues, despite the locker, such as the detent, 19. Thus, the micro-adjuster 20, including the micro-adjuster bearings 20a, allow for medical personnel to readjust the orientation of the front yoke 14 and the rear yoke 17 for the second adjustment, the second adjustment being after of the first adjustment. As also illustrated in FIGS. 3-6, the micro-adjuster 20 is associated with the yoke retainer 24 and rotatably associated with the front yoke 14, and the micro-adjuster 20 includes a release member 26, such as a screw or release button 26a, configured to releasably secure the front yoke 14 to the yoke retainer 24 to enable an angular rotation of the front yoke 14 and the rear yoke 17 in the second range of angular rotation relative to the cradle base 13. The micro-adjuster 20 is configured to enable the angular rotation of the front yoke 14 and the rear yoke 17 of the probe-holder 40 relative to the cradle base 13 in the second range of angular rotation, after the first adjustment, the angular rotation in the second range of angular rotation being indicated by the dashed arrowed lines B, the second range of angular rotation being less than the first range of angular rotation, by selective operation of the release member 26 to provide the second adjustment to further calibrate the cradle 1 for the medical procedure. The release member 26, such as including the screw or release button 26a, is configured for selective operation to enable the angular rotation for the second adjustment. The micro-adjuster 20, including the micro-adjuster bearings 20a, is associated with the yoke retainer 24 and in communication with the front yoke 14 and enables rotation of the front yoke 14 and the rear yoke 17 relative to the yoke retainer 24 when the yoke retainer 24 is positioned at the predetermined position at the predetermined angle, to selectively provide the second adjustment to further calibrate the cradle 1, the front yoke 14 being communicatively connected to the rear yoke 17, such as by association with the pivot side rail 22 and the lock side rail 23. Hence, an ultrasound probe can be held in the probe space 15, such as with respect to perpendicular locker detent 19, to an exact 90 degrees. Importantly, such second adjustment using the micro-adjuster 20 will allow medical personnel to expedite verification of needle grid alignment.

What is claimed is:

1. A cradle for holding a probe for imaging for a medical procedure, the cradle comprising:
    a base configured for securing the cradle to a stepper, the stepper being configured to be supported by a stabilizer;
    a locker associated with the base;
    a probe-holder rotatably supported on the base and having a probe space and being configured to receive a probe in the probe space, the probe-holder including:
        a rear yoke;
        a front yoke communicatively connected to the rear yoke, the front yoke and the rear yoke being configured to receive a probe, when the probe is positioned in the probe space, for the medical procedure; and
        a yoke retainer rotatably supporting the front yoke, and the yoke retainer and the rear yoke being rotatably supported on the base, and the base and the probe-holder being configured to enable the yoke retainer and the rear yoke to rotate in an angular rotation in a first range of angular rotation for a first adjustment to position the probe-holder at a predetermined position at a predetermined angle relative to the base by the probe-holder engaging the locker, to calibrate the cradle for the medical procedure, and being configured to enable the yoke retainer and the rear yoke to rotate in the first range of angular rotation to adjust a position of the probe-holder for the medical procedure; and
    a micro-adjuster associated with the yoke retainer and rotatably associated with the front yoke, the micro-adjuster including a release member configured to releasably secure the front yoke to the yoke retainer to enable an angular rotation of the front yoke and the rear yoke in a second range of angular rotation relative to the base, when the yoke retainer is positioned at the predetermined position at the predetermined angle, by selective operation of the release member, to provide a second adjustment after the first adjustment to position the front yoke and the rear yoke at a second position to further calibrate the cradle for the medical procedure, the second range of angular rotation being less than the first range of angular rotation.

2. The cradle of claim 1, further comprising:
    a plurality of bearings associated with the base, the plurality of bearings rotatably supporting the probe-holder on the base for the angular rotation in the first range of angular rotation.

3. The cradle of claim 1, wherein the release member comprises at least one of a screw or a release button configured for selective operation to enable the angular rotation in the second range of angular rotation for the second adjustment.

4. The cradle of claim 1, wherein the locker comprises a detent configured to locate a 90-degree position of the probe-holder relative to the base for the first adjustment.

5. The cradle of claim 1, further comprising:
    a latch movably associated with the probe-holder, the latch being configured to be positioned in engaging relation with the probe when the probe is positioned in the probe space and when the latch is in a closed position.

6. The cradle of claim 5, wherein the latch comprises a probe-lock-fixer, the probe-lock-fixer having a concave configuration to maximize a surface area of the probe-lock-fixer when in contact with the probe and configured to restrict angular movement of the probe when positioned in the probe space of the cradle.

7. The cradle of claim 6, wherein the concave configuration of the probe-lock-fixer has an eccentric profile.

8. The cradle of claim 1, further comprising:
    a latch including a probe-lock-fixer, the probe-lock-fixer being attached to the latch for fastening over the probe when the latch is in a closed position and configured to anchor the probe inside the probe space of the probe-holder.

9. The cradle of claim 1, wherein the probe-holder further comprises:
    a pivot side rail and a lock side rail communicatively connected to the front yoke and the rear yoke;
    a locking knob associated with the lock side rail; and
    a latch movably connected to the pivot side rail and configured for engagement with the locking knob to secure the probe, when the probe is positioned in the probe space, when the latch is in a closed position for the medical procedure.

10. The cradle of claim 9, wherein the release member comprises:
    a screw or a release button, the screw or the release button enabling the angular rotation in the second range of angular rotation for the second adjustment.

11. The cradle of claim 10, further comprising:
    a plurality of bearings associated with the base, the plurality of bearings rotatably supporting the probe-holder on the base for the angular rotation in the first range of angular rotation.

12. The cradle of claim 9, further comprising:
    a plurality of bearings associated with the base, the plurality of bearings rotatably supporting the probe-holder on the base for the angular rotation in the first range of angular rotation.

13. The cradle of claim 9, wherein the locker comprises a detent configured to locate a 90-degree position of the probe-holder relative to the base for the first adjustment.

14. The cradle of claim 13, wherein the release member comprises:
    a screw or a release button, the screw or the release button enabling the angular rotation in the second range of angular rotation for the second adjustment.

15. The cradle of claim 14, further comprising:
    a plurality of bearings associated with the base, the plurality of bearings rotatably supporting the probe-holder on the base for the angular rotation in the first range of angular rotation.

16. The cradle of claim 13, wherein the probe-holder further comprises:
    a capture knob mounted to the lock side rail configured to retain the locking knob from detaching from communicative engagement with the lock side rail.

17. The cradle of claim 13, wherein the latch further comprises:
    a probe-lock-fixer, the probe-lock-fixer being attached to the latch for fastening over the probe, when the latch is in a closed position, and being configured to anchor the probe inside the probe space of the probe-holder, the probe-lock-fixer having a concave configuration to maximize a surface area of the probe-lock-fixer in contact with the probe, when the probe is positioned in the probe-holder and the latch is in a closed position, to restrict angular movement of the probe in the cradle.

18. The cradle of claim 9, wherein the latch further comprises:
a probe-lock-fixer, the probe-lock-fixer being attached to the latch for fastening over the probe when the latch is in a closed position and configured to anchor the probe inside the probe space of the probe-holder.

19. The cradle of claim 18, wherein the probe-lock-fixer is configured in a concave configuration to maximize a surface area of the probe-lock-fixer in contact with the probe, when the probe is positioned in the probe-holder and the latch is in a closed position, and configured to restrict angular movement of the probe in the cradle.

20. The cradle of claim 19, wherein the probe lock fixer has an eccentric profile.

\* \* \* \* \*